United States Patent [19]

Sanfilippo et al.

[11] Patent Number: 5,430,219
[45] Date of Patent: Jul. 4, 1995

[54] INTEGRATED PROCESS FOR PRODUCING OLEFINS FROM METHANE-CONTAINING GAS MIXTURES

[75] Inventors: Domenico Sanfilippo; Stefano Rossini, both of Milan, Italy

[73] Assignees: Snamprogetti S.p.A.; Eniricerche S.p.A., both of Milan, Italy

[21] Appl. No.: 128,712

[22] Filed: Sep. 30, 1993

[30] Foreign Application Priority Data

Oct. 1, 1992 [IT] Italy .............. MI92A2280

[51] Int. Cl.$^6$ ................................. C07C 2/00
[52] U.S. Cl. ..................... 585/659; 585/310; 585/633; 585/658; 585/500
[58] Field of Search ............... 585/700, 654, 661, 310, 585/633, 659

[56] References Cited

U.S. PATENT DOCUMENTS

| | | | |
|---|---|---|---|
| 3,716,545 | 2/1973 | Ripley | 585/622 |
| 3,737,473 | 6/1973 | Ripley | 585/622 |
| 3,829,524 | 8/1974 | Senn, III et al. | 585/659 |
| 3,904,703 | 9/1975 | Lo et al. | 585/633 |
| 4,751,339 | 6/1988 | Jezl et al. | |
| 5,015,799 | 5/1991 | Walker et al. | 585/661 |
| 5,143,886 | 9/1992 | Iezzi et al. | |
| 5,312,795 | 5/1994 | Kaminsky et al. | 502/349 |

*Primary Examiner*—Anthony McFarlane
*Attorney, Agent, or Firm*—Oblon, Spivak, McClelland, Maier & Neustadt

[57] ABSTRACT

Disclosed is an integrated process for producing olefins by starting from methane containing gas mixture, which process essentially comprises the following steps:

converting methane into higher hydrocarbons by oxidative coupling carried out in the presence of air and/or oxygen;

dehydrogenating, with the aid of a catalyst, said higher hydrocarbons, with an olefin-rich mixture being obtained;

removing $H_2O$, $CO_2$, $CO$ and $H_2$ from the resulting olefinic mixture;

removing from said olefinic mixture any not converted methane, and recycling it upstream from the oxidating coupling;

separating ethylene from the olefinic mixture;

separating any not dehydrogenated ethane from the olefinic mixture.

15 Claims, 2 Drawing Sheets

INTEGRATED PROCESS FOR PRODUCING OLEFINS FROM METHANE-CONTAINING GAS MIXTURES

The present invention relates to an integrated process for producing olefins by starting from methane containing gas mixtures, in particular from natural gas.

The range of industrial uses of compounds containing a plurality of carbon atoms is extremely wide. The sources of carbon atoms are three: petroleum, presently the major source (petrochemistry); natural gas, whose main component is, by far, methane, and which is very often found together with petroleum; and coal.

Apart from the higher components present in a wet natural gas, which can be used as such, the industrial-chemical exploitation of methane and coal requires that a backbone of at least two carbon atoms is built and a reactivity site, e.g., a double bond, is introduced: therefore, the matter is of converting them into at least ethylene.

A feasible route for such an upgrading is through syngas preparation. In such a way, mixtures of various kinds of higher (i.e., containing two or more carbon atoms) paraffinic and olefinic hydrocarbons can be obtained according to the so-said "Fischer-Tropsch" reaction, and its subsequent modifications, over catalysts of Fe, Co, Ni, as such, or as mixtures and variously modified. According to another route, syngas can be converted into methanol over Cu-, Zn-, Al-, Cr-based catalysts of oxide character ("oxidic catalysts"), according to widely used technologies on industrial scale, and methanol can be converted, in its turn, into olefins, over zeolitic materials according to the MTO process.

The basic problem displayed by the above mentioned processes is the same syngas preparation, which is economically penalizing. Being able to obtain ethylene directly from the primary source of carbon atoms without having to resort to intermediate syngas preparation, is regarded as a goal of the highest interest. Whilst such a direct route appears to be impossible in the case of coal, methane can be caused to advantageously react with air (oxygen) on oxidic catalysts, with mixtures of hydrocarbons of two or more carbon atoms being obtained: such a reaction is known as "oxidative coupling".

Inside each fraction containing "n" carbon atoms, the paraffinic component is generally prevailing over the olefinic one. Only by operating with long contact times, at the highest operating temperatures reported for oxidative coupling, i.e., 850°-950° C., and in the presence of larger oxygen amounts, olefins can be obtained in an amount which is equal to, or slightly larger than, as of the corresponding paraffin.

Unfortunately, a long contact time means poor throughput values per catalyst volume (or mass) unit and time unit, whilst larger amounts of oxygen generate, in the presence of a higher methane conversion rate, a lower selectivity to hydrocarbons for oxidative coupling reaction.

According to an alternative process, it was found that the addition of volatile, chlorine-containing organic compounds can favour the formation of ethylene from ethane. The presence of such chlorinated compounds implies the presence of chlorine in the end product. Such a presence would considerably limit the possible use of olefins owing to material specification and corrosion problems.

The present Applicants have found now a process which makes it possible the olefin/paraffin ratio to be considerably increased in each fraction of "n" carbon atoms, where "n" is to be understood as mostly being equal to two and three, and sometimes, also four, obtained by combining a typical first step of oxidative coupling, with a second step, of catalytic dehydrogenation.

The integrated process for producing olefins by starting from gas mixtures containing methane, which is the subject matter of the present invention, is characterized in that said integrated process essentially comprises the following steps:

converting methane into higher hydrocarbons by oxidative coupling carried out in the presence of air and/or oxygen with a molar ratio of $CH_4/O_2$ selected within the range of from 1 to 100, preferably of from 1.5 to 20, at a temperature comprised within the range of from 500° to 1000° C., preferably of from 700° to 950° C., under a pressure comprised within the range of from 0.01 to 10 atm, preferably of from 5.0 to 5 atm and during a contact time comprised within the range of from 0.01 to 10 seconds, preferably of from 0.03 to 3.6 seconds;

dehydrogenating, with the aid of a catalyst, said higher hydrocarbons, at a temperature comprised within the range of from 400° to 950° C., preferably of from 500° to 800° C., under a pressure comprised within the range of from 0.01 to 10 atm and during a contact time comprised within the range of from 0.01 to 50 seconds, preferably of from 0.1 to 20 seconds, with an olefin rich mixture being obtained;

removing $H_2O$, $CO_2$ and $H_2$ from the resulting olefinic mixture;

removing from the olefinic mixture any not converted methane, and recycling it upstream from the oxidating coupling step;

separating ethylene from the olefinic mixture;

separating from the olefinic mixture any non-dehydrogenated ethane, possibly recycling it downstream from the oxidative coupling step and upstream from the dehydrogenation step;

possibly, subdividing, in one or more steps, the heavier hydrocarbons remaining in the mixture, so as to obtain paraffinic hydrocarbons containing three or more carbon atoms, which can be at least partially recycled upstream from the dehydrogenation step; and olefinic hydrocarbons containing three or more carbon atoms.

The fresh, methane containing feedstock can be fed upstream from the oxidative coupling step, or downstream from the oxidative coupling step and upstream from the dehydrogenation step, according to the contained amount of methane: feeding said fresh feedstock upstream from the oxidative coupling step is recommended when said fresh feedstock is a natural gas essentially constituted by methane; the downstream feed is recommended when the fresh feedstock is a wet natural gas containing hydrocarbons with two or more carbon atoms.

Furthermore, recycling at least a portion of $H_2O$ removed from the olefinic mixture and/or at least a portion of $CO_2$ removed from the olefinic mixture upstream from the oxidative coupling step, might prove to be advantageous.

Recycling $CO_2$ increases the selectivity to hydrocarbons in the oxidative coupling step, by at least 15%, however to the damage of the ratio of $C_2=/C_2$, which is anyway restored by the dehydrogenation.

Recycling $H_2O$ slightly increases the selectivity to hydrocarbons in the oxidating coupling step without any negative outcomes on $C_2=/C_2$ ratio; such a ratio can be then increased by the dehydrogenation.

The methane conversion step (oxidative coupling) can be carried out by taking advantage of the catalysts already known from the prior art, such as, e.g., those as disclosed in patent application IT-19284 A90, to the same Applicants, which catalysts contain:

an element selected from Ge, Si, Sn, Ti, Zr;
an element selected from La, Sc, Y;
an alkali or alkaline-earth metal.

The dehydrogenation by means of a catalyst can be either a catalytic dehydrogenation with hydrogen formation, or an oxidative catalytic dehydrogenation.

The catalytic dehydrogenation with hydrogen formation, of olefins with a small number of carbon atoms is being currently operated at an industrial level for the hydrocarbons of $C_4$ cut, mainly isobutane, according to the technologies developed by Snamprogetti, Oleflex, Houdry.

By means of the same technologies, also ethane and propane can be processed by suitably changing the operated conditions, in order to obtain the corresponding olefins.

Useable catalysts for the oxidative catalytic dehydrogenation are those known from the prior art, e.g., that catalyst which is described in the proceedings of the "Symposium on Natural Gas Upgrading II", S. Francisco, (1992), page 200 (Fereira P. R., De Gouveia V., Rosa F.).

The present Applicants have furthermore surprisingly found that by using suitable dehydrogenation catalysts, in the second step of the process according to the present invention, the reaction of dehydrogenation into olefins of the paraffins contained in the effluent leaving the oxidative coupling step can be obtained with the possible competitive reactions, such as steam reforming, water gas shift, and so forth, being kept to the very minimum.

Said suitable catalysts are those as disclosed in Italian patent applications IT-21 180 A85, IT-19 283 A90 and IT-MI 92A 000 556 to the same Applicant.

By selecting said catalysts, the catalytic dehydrogenation with hydrogen formation appears to yield optimal results, because it is not affected by the presence of methane which, within most operating range, can be regarded as an inert accompanying species. Suitable process designs make it furthermore possible wet natural gases (i.e., containing $C_2$, $C_3$, and so forth, hydrocarbons) to be treated without having to resort to specific separation lines for hydrocarbons different from methane, and upgrading such higher components as olefins.

In the first patent application (IT-21 180 A85), the used catalyst is based on aluminum, chromium, potassium and silicon; the preparation of said catalyst starts from aluminum oxide in microsphere form, which is first ignited at temperatures comprised within the range of from 500° to 700° C., then at temperatures higher than 1000° C. for many hours, then the resulting calcined product is impregnated with a solution containing chromium and potassium compounds, or separate solutions of said coumpound, is dried, and is impregnated again with a solution containing a silicon compound, and finally is dried and ignited once more at temperatures of up to 700° C.

In the second patent application, a catalytic composition is claimed which is formed by:

platinum in an amount of from 0.1 to 3% by weight;
possibly tin, in an amount of from 0 to 1.5% by weight;
a carrier selected from titanated alumina, titanated silica and/or titanium silicalite, in which the titanium amount in the same carrier is comprised within the range of from 0.05 to 3% by weight.

In the third patent application, catalytic compositions are disclosed which contain gallium, alumina, possibily silica and/or one or more alkali or alkaline-earth metals, which are activated by means of a thermal activation in air at a temperature comprised within the range of from 450° to 1000° C., followed by a post-activation carried out by means of the following steps:

oxidation with air and/or oxygen, or a mixture containing at least 5% by volume of oxygen, in an inert gas, during a time comprised within the range of from 1 to 180 minutes, at a temperature comprised within the range of from 500° to 1000° C. and preferably during a time comprised within the range of from 30 to 90 minutes;
washing with an inert gas during a time comprised within the range of from 1 to 10 minutes;
reduction with hydrogen or a mixture containing at least 10% by volume of hydrogen, and an inert or reducing gas, during a time comprised within the range of from 1 to 120 minutes and at a temperature comprised within the range of from 450° to 800° C.

In particular, preferred catalytic composition in said patent application contains:

gallium in an amount comprised within the range of from 0.1 to 33.6% by weight (when expressed at $Ga_2O_3$),
silica in an amount comprised within the range of from 0.08 to 3% by weight,
possibly one or more alkali or alkaline-earth metals in an amount comprised within the range of from 0 to 5% by weight,
alumina, the balance to 100, as delta or theta phase, or as a mixture of delta+theta or delta+theta+alpha phases.

The claimed process is disclosed now with the aid of the two accompanying figures.

DETAILED DESCRIPTION OF THE DRAWINGS

Figure 1:
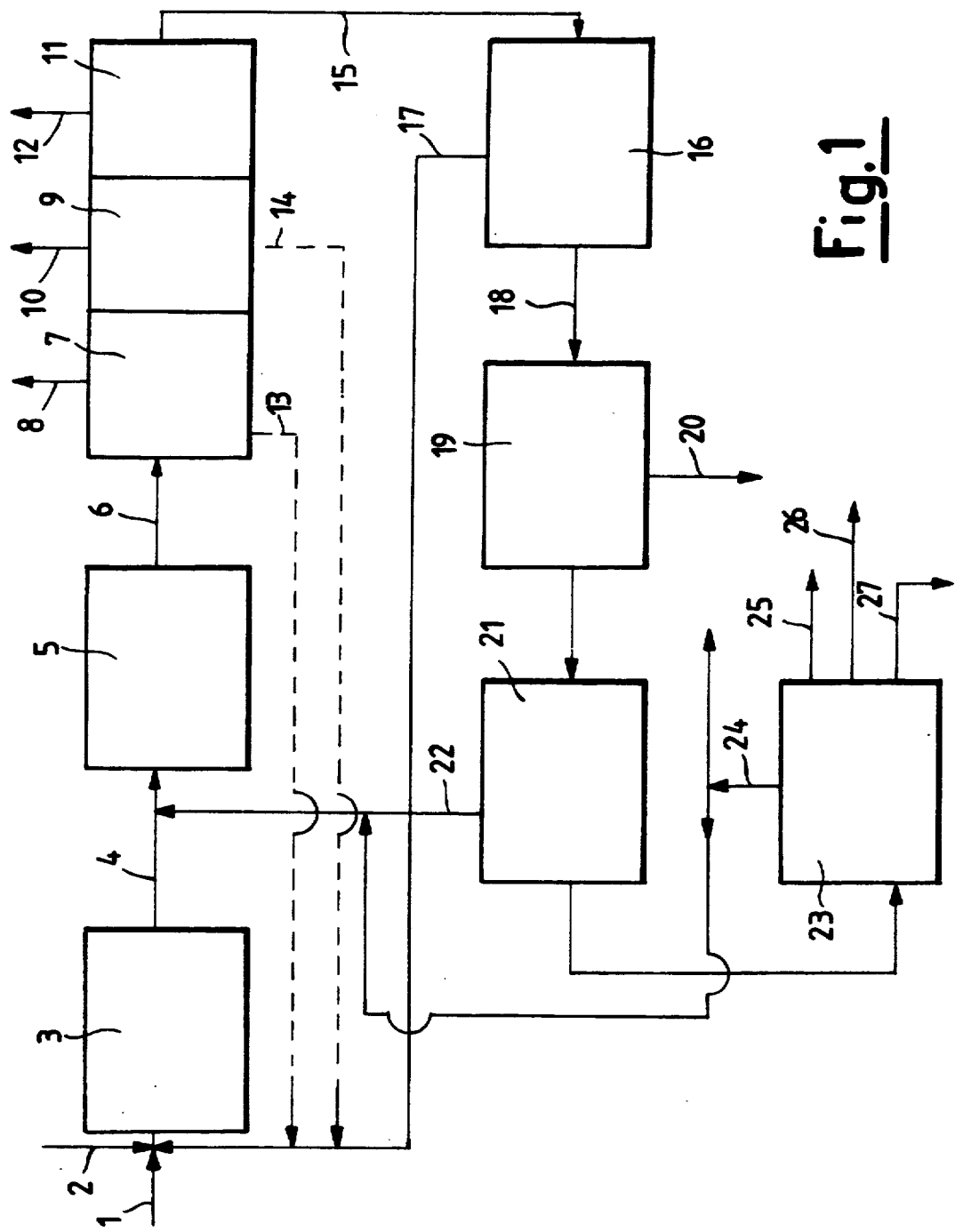
FIGS. 1 and 2 disclose flow diagrams of the inventive process.

In the flow diagram of FIG. 1, the fresh feedstock mainly containing methane (1) is mixed with the oxidizer (2) (air and/or oxygen) and recycled methane (17) and, inside reactor (3), is converted, by oxidative coupling, into higher hydrocarbons.

The effluent (4) from the reactor, admixed with any possibile recycled ethane (22) and propane (24) is fed to the dehydrogenation reactor (5), in which the higher paraffinic hydrocarbons are then catalytically dehydrogenated in such a way as to obtain a stream which is richer of olefins (6).

From such a stream (6), $H_2O$ (8) is first removed, in the step (7), then in the step (9) $CO_2$ (10) is removed, and finally, in (11), CO and $H_2$ (12) are removed.

A portion of H₂O (13) and a portion of CO₂ (14) can possibly be recycled upstream from the oxidative coupling step (3).

The purified olefinic Stream (15) is sent to a separator (16) in order to recover any unconverted methane (17), to be recycled upstream from the oxidative coupling step (3).

Said mixture from which methane was removed (18) is separated, in (19), from ethylene (20); then, in (21), is separated from ethane (22); and finally, in (23), is subdivided into a stream essentially containing propane (24), a stream essentially containing C₃ olefins (25), a stream mainly containing C₄ olefins (26), and a stream containing C₄ paraffins (27).

According to the cases, the paraffinic streams [ethane (22), propane (24), C₄ paraffins (27)] can be either partially or totally recycled upstream from the catalytic dehydrogenation reactor (5).

Figure 2:
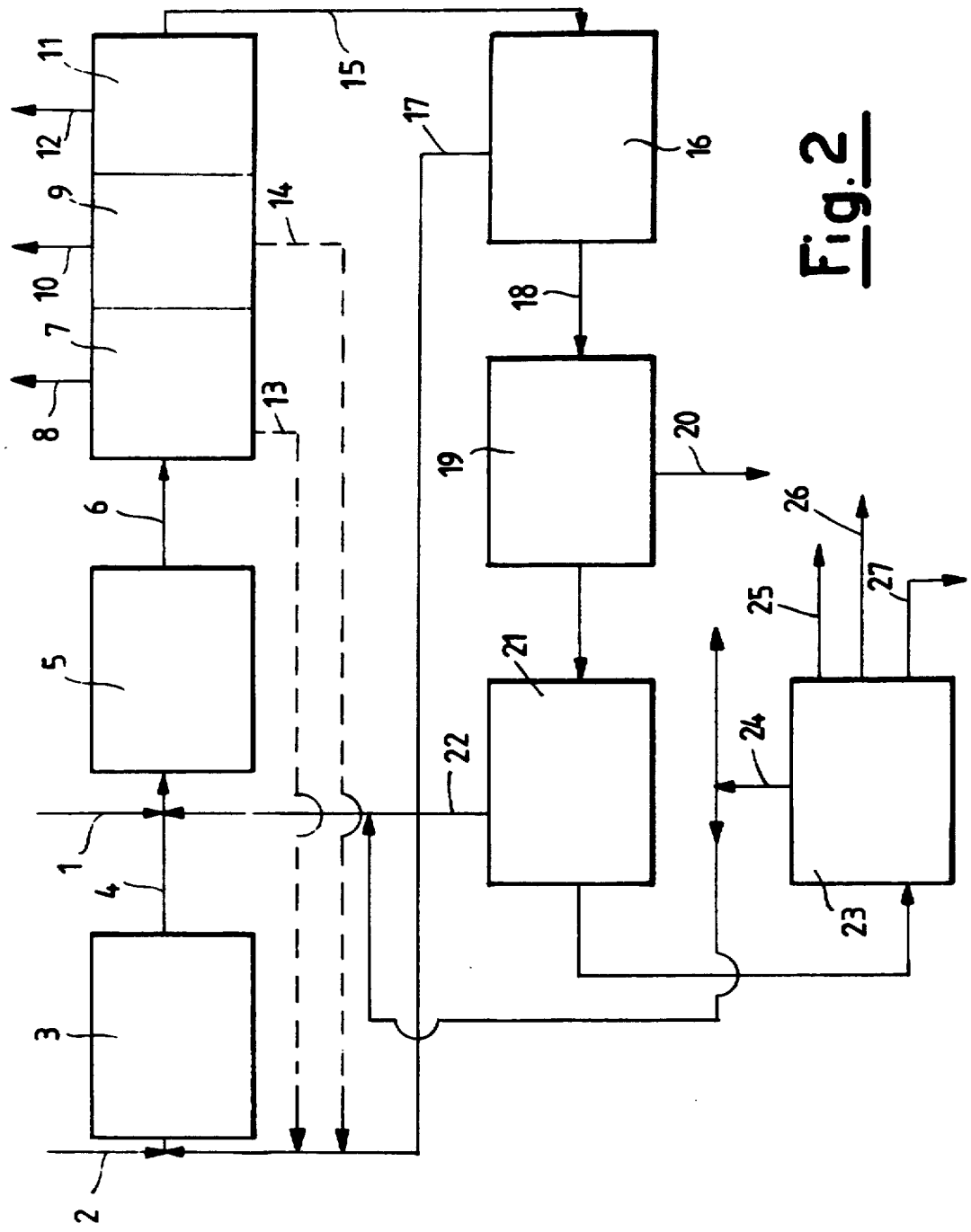

The flow diagram of FIG. 2 is substantially analogous to the flow diagram of FIG. 1, but for the feed of the methane containing feedstock not taking place upstream from the oxidative coupling step, but, on the contrary, downstream from it and upstream from the catalytic dehydrogenation step (5).

This second operating modality is preferred when the fresh feedstock is a wet gas: in such a way, it is not necessary that methane is separated from C₂⁺ fractions and the latter are upgraded by transforming their paraffinic fraction into the corresponding olefin.

Some examples are given now order to better illustrate the invention.

EXAMPLES 1-19

Some tests were carried out in the laboratory, always by starting from a feedstock which essentially contained methane, by adopting the operating modality of FIG. 1, without recycling the ethane (22) separated from the olefinic mixture downstream from the conversion step, and using the following catalytic systems for the conversion:

* Zr:La:Na = 1:1:1, by mol;
and, as regards the dehydrogenation:
   the catalytic dehydrogenation (Examples 1, 2, 4, 5, 7, 8, 10):
   Al:Cr:K:Si = 5:1:0.1:0.1, by mol;
   oxidative dehydrogenation (Example 18):
   MnO₂ 10% w; Na₂O 0.5.% w; SiO₂ 89.5% w
   (% w = percent by weight).

In Examples 1, 2, 4, 5, 7, 8, 10, 18, the streams of H₂O (13) and CO₂ (14) were not recycled, whilst in Example 12 only CO₂ (34% by volume) was recycled to the oxidative coupling step; and, in Example 15, only H₂O (20% by volume) was recycled to the oxidative coupling step.

Examples 3, 6, 9, 13, 14, 16, 17, 19 are comparison examples, because in these examples the dehydrogenation step was not carried out, with only the oxidative coupling step being carried out, by using the same catalytic system; in particular, in the comparison Examples 3, 6, 9, 13, 16, 19 the streams of H₂O and CO₂ were not recycled, whilst in the comparison Examples 14 and 17, the recycled streams are analogous to those as of the corresponding Examples 12 and 15.

The obtained results are reported in Table I.

TABLE I

| Example | C₁/O₂ ratio | $t_c$ seconds | $T_c$ °C. | $t_d$ seconds | $T_d$ °C. | CH₄ content, (%) | $C_2^=/C_2$ ratio | CO₂ Volume, (%) | H₂O Volume, (%) |
|---|---|---|---|---|---|---|---|---|---|
| 1 | 10 | 0.2 | 800 | 1.0 | 725 | 12.8 | 0.90 | — | — |
| 2 | 10 | 0.2 | 820 | 2.0 | 745 | 10.2 | 4.22 | — | — |
| 3 | 10 | 0.2 | 800 | — | — | 14.0 | 0.60 | — | — |
| 4 | 10 | 0.5 | 800 | 1.0 | 735 | 11.6 | 1.56 | — | — |
| 5 | 10 | 0.5 | 800 | 2.5 | 742 | 10.7 | 2.78 | — | — |
| 6 | 10 | 0.5 | 800 | — | — | 12.5 | 0.80 | — | — |
| 7 | 5 | 0.5 | 800 | 1.0 | 750 | 19.6 | 1.54 | — | — |
| 8 | 5 | 0.5 | 800 | 5.0 | 760 | 18.5 | 4.50 | — | — |
| 9 | 5 | 0.5 | 800 | — | — | 22.0 | 0.93 | — | — |
| 10 | 5 | 1.0 | 800 | 2.0 | 755 | 18.0 | 2.90 | — | — |
| 11 | 5 | 0.5 | 800 | — | — | 21.8 | 1.01 | — | — |
| 12 | 5 | 1.04 | 750 | 2.5 | 745 | 18.1 | 3.02 | 34 | — |
| 13 | 5 | 1.5 | 750 | — | — | 21.5 | 1.02 | — | — |
| 14 | 5 | 1.02 | 750 | — | — | 19.0 | 0.96 | 34 | — |
| 15 | 5 | 1.15 | 750 | 2.5 | 753 | 18.4 | 2.94 | — | 20 |
| 16 | 5 | 1.34 | 750 | — | — | 19.2 | 0.74 | — | — |
| 17 | 5 | 1.15 | 750 | — | — | 19.5 | 0.76 | — | 20 |
| 18 | 5 | 0.4 | 800 | 3.0 | 675 | 18.2 | 3.90 | — | — |
| 19 | 5 | 0.4 | 800 | — | — | 19.1 | 0.70 | — | — |

$t_c$ = Contact time in the oxidative coupling step
$t_d$ = Contact time in the dehydrogenation step
$T_c$ = Temperature in the oxidative coupling step
$T_d$ = Temperature in the dehydrogenation step

We claim:
1. A process for producing olefins from a methane containing gas mixture comprising the steps of:
   converting methane in said methane containing gas mixture into higher hydrocarbons by oxidative coupling in the presence of air and/or oxygen at a molar ratio of CH₄/O₂ of 1:1 to 100:1, at a temperature of 500° to 1,000° C., at a pressure of 0.01 to 10 atm. and at a contact time of 0.01 to 10 seconds,
   catalytically non-oxidatively dehydrogenating said higher hydrocarbons with hydrogen formation at a temperature of 400° to 950° C., at a pressure of 0.01 to 10 atm. and at a contact time of 0.01 to 50 seconds to obtain a mixture comprising the corresponding olefins,
   removing H₂O, CO₂ and H₂ from the resulting olefinic mixture,
   removing unconverted methane from said resulting olefinic mixture and recycling it to said oxidative coupling step,
   separating ethylene and/or propylene from said resulting olefinic mixture,
   and separating any non-dehydrogenated hydrocarbon from said olefinic mixture.

2. Process according to claim 1, in which the oxidative coupling is carried out with a molar ratio of $CH_4/O_2$ comprised within the range of from 1.5 to 20, at a temperature comprised within the range of from 700° to 950° C., under a pressure comprised within the range of from 0.5 to 5 atm, and during a contact time comprised within the range of from 0.03 to 3.6 seconds.

3. Process according to claim 1, in which the dehydrogenation with the aid of a catalyst is carried out at a temperature comprised within the range of from 500° to 800° C., during a contact time comprised within the range of from 0.01 to 20 seconds.

4. Process according to claim 1, in which, after ethane separation, the heavier hydrocarbons remaining in the mixture are subdivided, in one or more steps, so as to obtain paraffinic hydrocarbons with three or more carbon atoms, which, at least partially, can be recycled upstream from the dehydrogenation step, and olefinic hydrocarbons with 3 or more carbon atoms.

5. Process according to claim 1, in which the ethane separated from the olefinic mixture is recycled downstream from the oxidative coupling and upstream from the dehydrogenation step.

6. Process according to claim 1, in which the methane containing gas mixture is fed upstream from the oxidative coupling.

7. Process according to claim 6, in which the gas mixture is a natural gas essentially constituted by methane.

8. Process according to claim 1, in which the methane containing gas mixture is fed downstream from the oxidative coupling and upstream from the dehydrogenation step.

9. Process according to claim 7, in which the gas mixture is a wet natural gas containing hydrocarbons with 2 or more carbon atoms.

10. Process according to claim 1, in which at least a portion of removed $H_2O$ is recycled upstream from the oxidative coupling step.

11. Process according to claim 1 in which at least a portion of the removed $CO_2$ is recycled upstream from the oxidative coupling step.

12. The process according to claim 1, wherein said oxidative coupling is carried out with a catalyst comprising:
   an element selected from the group consisting of Ge, Si, Sn, Ti and Zr,
   an element selected from the group consisting of La, Sc and Y, and
   an alkali or alkaline-earth metal;
   and said catalytic dehydrogenation with hydrogen formation is carried out with a catalyst selected from the group consisting of:
   a. Al, Cr, K and Si; or
   b. 0.1 to 3% by weight Pt and 0 to 1.5% by weight Sn on a carrier of titanated alumina, titanated silica and/or titanium-silicate, the titanium in the carrier being from 0.05 to 3% by weight; and
   c. 0.1 to 33.6% by weight Ga, expressed as $Ga_2O_3$, 0.08 to 3% by weight silica, 0 to 5% by weight alkali or alkaline-earth metals,
   balance alumina as delta phase or theta phase, or as a mixture of delta and theta and alpha phases.

13. The process according to claim 12, wherein said catalytic dehydrogenation with hydrogen formation is carried out with defined catalyst a.

14. The process according to claim 12, wherein said catalytic dehydrogenation with hydrogen formation is carried out with defined catalyst b.

15. The process according to claim 12, wherein said catalytic dehydrogenation with hydrogen formation is carried out with defined catalyst c.

* * * * *